United States Patent [19]
Burd et al.

[11] Patent Number: 5,186,844
[45] Date of Patent: Feb. 16, 1993

[54] APPARATUS AND METHOD FOR CONTINUOUS CENTRIFUGAL BLOOD CELL SEPARATION

[75] Inventors: Tammy L. Burd, Fremont; Carol T. Schembri, San Mateo, both of Calif.

[73] Assignee: Abaxis, Inc., Mountain View, Calif.

[21] Appl. No.: 678,762

[22] Filed: Apr. 1, 1991

[51] Int. Cl.[5] .............................................. B01D 21/26
[52] U.S. Cl. ................................ 210/782; 210/95;
    210/198.1; 210/380.1; 210/514; 210/532.1;
    210/789; 422/72; 422/101; 422/1; 436/45;
    436/63; 436/177; 436/180; 494/27; 494/34;
    494/43
[58] Field of Search ............ 210/94, 95, 198.1, 380.1,
    210/407, 514, 512.1, 515, 532.1, 782, 787, 789;
    422/64, 72, 101, 102; 436/45, 63, 177, 180;
    494/16, 17, 27, 29, 37, 43

[56] References Cited

U.S. PATENT DOCUMENTS

| | | | |
|---|---|---|---|
| 3,899,296 | 8/1975 | Mailen et al. | 422/72 |
| 3,901,658 | 8/1975 | Burtis et al. | 422/72 |
| 4,279,862 | 7/1981 | Bretaudiere et al. | 422/72 |
| 4,284,602 | 8/1981 | Kelton et al. | 422/72 |
| 4,314,968 | 2/1982 | Guigan | 422/64 |
| 4,350,283 | 9/1982 | Leonian | 422/72 |
| 4,356,958 | 11/1982 | Kolobow et al. | 494/45 |
| 4,381,072 | 4/1983 | Matsumoto et al. | 494/10 |
| 4,419,089 | 12/1983 | Kolobow et al. | 494/45 |
| 4,463,097 | 7/1984 | Guigan | 436/45 |
| 4,680,025 | 7/1987 | Kruger et al. | 604/6 |
| 4,708,712 | 11/1987 | Mulzet | 494/45 |
| 4,740,472 | 4/1988 | Burtis et al. | 210/787 |
| 4,776,964 | 10/1988 | Schoendorfer et al. | 210/782 |
| 4,788,154 | 11/1988 | Guigan | 210/787 |
| 4,847,205 | 7/1989 | Burtis et al. | 436/45 |
| 4,876,203 | 10/1989 | Guigan | 436/45 |
| 4,894,204 | 1/1990 | Cornut | 422/72 |
| 4,999,304 | 3/1991 | Robertson | 436/177 |

Primary Examiner—W. Gary Jones
Attorney, Agent, or Firm—Townsend and Townsend

[57] ABSTRACT

An analytical rotor for separating cellular components from a biological fluid includes a separation chamber spaced radially outward from a sample chamber. The sample chamber may be an open receptacle disposed to receive sample or may be a mixing chamber which receives sample and diluent. A flow restrictive channel connects the sample chamber to the separation chamber so that fluid enters the separation chamber at a controlled rate. The cellular components collect within a retention region located generally at the outer periphery of the collection chamber while cell-free fluid is continuously removed through a collection port. The collection port is spaced annularly apart from the flow channel so that there is sufficient residence time within the separation chamber for substantially complete separation of the cells from the fluid fraction. In a first embodiment, a collection chamber is attached through the collection port through an annular flow channel, while in a second embodiment a collection chamber is connected through a vertical flow channel.

44 Claims, 2 Drawing Sheets

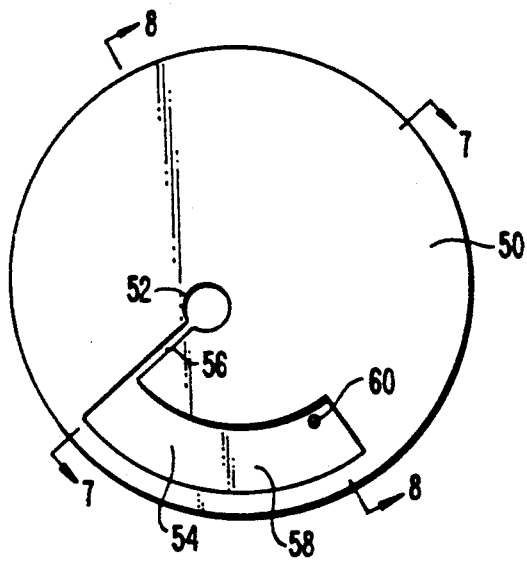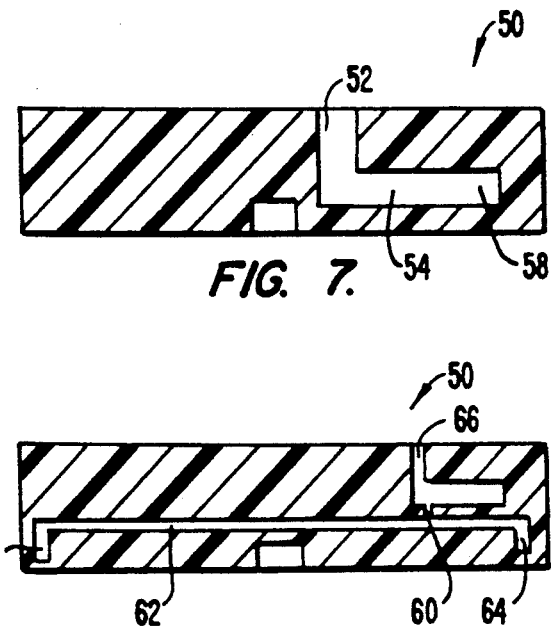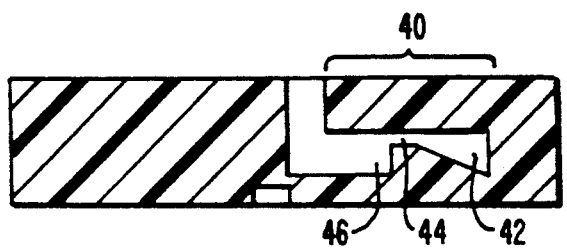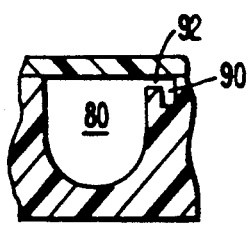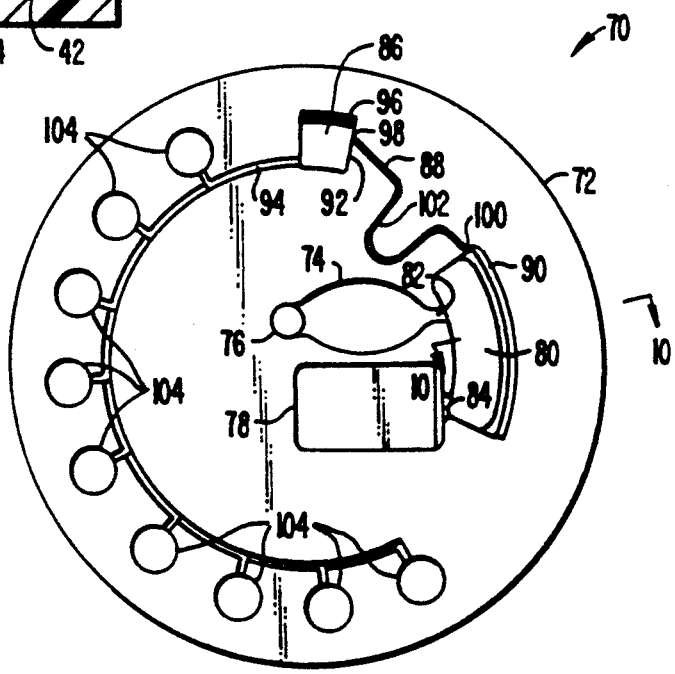

5,186,844

APPARATUS AND METHOD FOR CONTINUOUS CENTRIFUGAL BLOOD CELL SEPARATION

The present invention is related to application Ser. No. 07/532,524, application Ser. No. 07/678,823, and application Ser. No. 07/678,824 the disclosures of which are incorporated herein by reference.

BACKGROUND OF THE INvENTION

1. Field of the Invention

The present invention relates generally to apparatus and methods for separating cellular components from biological fluids and, more particularly, to the design and use of a centrifugal rotor which is capable of continuously separating plasma from an applied volume of whole blood as the rotor is spun.

Analytical testing of biological fluids frequently requires that cellular components be separated from the fluid in order to provide a red blood cell-free fluid fraction for analysis. For example, many blood tests require removal of blood cells so that analysis can be performed on the remaining blood plasma. A common method for achieving such cellular removal employs a analytical rotor where the relatively dense cellular components are centrifugally separated from the less dense blood plasma. Frequently, the resulting blood plasma undergoes a detection reaction, e.g., an immunological or enzymatic reaction, and subsequent optical analysis within the analytical rotor.

Heretofore, most analytical rotors for separating cellular components from biological fluids have been designed for batch-type separation. In batch separation, a discrete volume of the biological fluid is applied to the rotor, and the rotor then spun to separate the entire applied fluid volume into a cellular fraction and a cell-free fluid fraction prior to performing any reaction or optical analysis. Usually, the cell-free fluid fraction will first be collected within a collection compartment or chamber and only after the entire volume is collected, the fraction will be transferred to a separate region within the rotor in order to perform a reaction or other analytic procedure.

The need to completely separate cellular components from the biological fluid prior to analysis, however, is disadvantageous in several respects. First, the initial separation step can be time-consuming and significantly delay the initiation of subsequent steps in the analysis, e.g., reaction with immunological reagent(s) and/or optical examination. Second, the need to transfer cell-free fluid within the rotor after the initial separation is complete usually requires additional step(s) in the analytical protocol. Such additional step(s) complicate the protocol and further increase the time required to perform the analysis. In automated testing systems, even small time delays and minor complications of the analytical protocol can greatly decrease the efficiency of the test being performed.

For these reasons, it would be desirable to provide improved analytical rotors and methods for separating cellular components from biological fluids, where the separation can be achieved continuously and simultaneously with transfer of cell-free fluid to a separate region within the rotor wherein the fluid can be subjected to an analytical reaction or optical examination, or both. In particular, it would be desirable to be able to initiate transfer of the cell-free fluid into a collection chamber or chambers where analytical reactions and/or analyses can begin even while the rotor continues to spin and before the entire biological fluid volume has been separated. It would further be desirable to be able to combine and mix diluents with the biological fluid as a part of the separation protocol.

2. Description of the Background Art

U.S. Pat. No. 4,708,712, describes a rotor intended for continuous plasma separation for use in therapeutic procedures, such as plasmapheresis. The rotor includes an eccentrically disposed channel which receives blood through an inlet port. The channel is positioned so that it has a decreasing radius relative to the axis of rotation in the clockwise direction from the inlet port and an increasing radius in the counterclockwise direction. Whole blood entering the channel from the inlet will separate into a lighter fraction (including plasma and platelets) which flows in the clockwise direction in a heavier fraction (including plasma and blood cells) which flows in the counterclockwise direction. The blood cells are collected in a dam region which is located in a maximum radial distance from the axis. U.S. Pat. Nos. 4,419,089 and 4,356,958, disclose the concept of using eccentric or spiral channels for separating blood cells from plasma by centrifugation. U.S. Pat. No. 3,899,296, discloses a separation chamber within an analytical rotor, where plasma is removed by aspiration rather than by continued centrifugation. U.S. Pat. No. 4,894,204, discloses the use of a siphon structure to hold liquid in a rotor receptacle. See also U.S. Pat. Nos. 3,901,658; 4,279,862; 4,284,602; 4,314,968; 4,350,283; 4,381,072; 4,463,097; 4,680,025; 4,776,964; 4,847,205; and 4,876,203, which relate to the construction and use of various devices for separating cells from blood and other biological fluids.

SUMMARY OF THE INVENTION

According to the present invention, an analytical rotor for separating cellular components from a cell-containing biological fluid comprises a rotor body having a sample chamber and a separation chamber formed therein. The separation chamber is located radially outward from the sample chamber and connected thereto by a flow restrictive channel. Thus, biological fluid which is introduced to the sample chamber will flow radially outward into the separation chamber as the rotor is spun. The dimensions of the flow restrictive channel are selected to provide a desired flow rate into the separation chamber when the rotor is spun at a predetermined speed.

The sample chamber may be a sample receptacle having an inlet opening or port which allows the user to introduce a volume of sample to be tested. Alternatively, the sample chamber may be a mixing chamber which receives sample from a sample chamber and diluent from a diluent chamber. Optionally, such a mixing chamber may include a cell retention region at or near its radially outward periphery.

The separation chamber will have dimensions selected to allow cellular components to separate from the biological fluid as the fluid continuously flows toward a means for collecting cell-free fluid within the chamber. Typically, the separation chamber will be annularly elongated with the flow restrictive channel located at or near one annular extremity and the means for collecting cell free fluid located at or near the opposite annular extremity. In this way, the separation chamber provides a sufficiently long flow path so that the residence time of the biological fluid (i.e., the time prior to the collection of cell-free fluid) is adequate to allow the cellular components to migrate radially outward into a retention region which is located at the radially outward periphery of the separation chamber.

In the specific embodiments, the cell free fluid collection means may be an annular channel which allows the cell-free fluid to overflow into one or more annularly-spaced apart collection chambers. Conveniently, the collection chamber may be an analysis chamber, e.g., a cuvette, to allow in situ analysis of the fluid and may contain reagents which facilitate detection of an analyte or performance of another analytical procedure. Alternatively, the cell-free fluid collection mean may be an axially or vertically oriented passageway which allows cell-free fluid to pass into a collection chamber which is disposed beneath the separation chamber. In the latter case, the collection chamber may be fluidly connected with a plurality of peripherally spaced-apart cuvettes where the desired analytical procedure is performed.

In a preferred embodiment, the separation chamber will include a capillary barrier which divides the cell retention region from the fluid flow path between the flow restrictive channel and the cell-free fluid collection means. In this way, the cells which pass into the retention region as the rotor is spun may be retained within the retention region even during subsequent handling of the rotor.

In a further preferred embodiment of the present invention, the rotor will contain a plurality of sample receptacles, separation chambers, and optionally mixing chambers and collection chambers. In this way, multiple blood samples may be simultaneously separated and optionally analyzed with all cellular separation steps being performed simultaneously.

In a still further preferred embodiment, the flow rate restrictive channel will include a siphon structure having a path which extends radially inward and which (prior to "priming") prevents flow from the sample chamber into the separation chamber while the rotor is spinning. The use of such a siphon barrier is particularly advantageous in embodiments which employ a mixing chamber to allow initial introduction of sample and diluent without carryover into the separation chamber.

In an alternate embodiment, the mixing chamber may be sufficient to provide a desired level of separation without a separation chamber. The provision of a flow restrictive outlet on the mixing chamber allows a sufficient fluid residence time within the mixing chamber so that the cellular components of the fluid can be separated radially outward into a retention region as the rotor is spun.

According to the method of the present invention, the cell-containing biological fluid is introduced to the receptacle region within the analytical rotor. Spinning of the rotor causes a radially outward flow of the biological fluid through the flow restrictive channel into the separation chamber. Within the separation chamber, continued spinning of the rotor causes cellular components of the fluid to migrate radially outward into the retention region at the periphery of the chamber where they are entrapped. The resulting cell-free fluid, in contrast, flows along a flow path which is radially inward from the retention region and is continuously removed from the separation chamber through the collection means which is located at a position annularly spaced-apart from the flow channel entry point. In this way, sufficient residence time is provided so that the cellular components may be substantially completely separated prior to removal of the fluid fraction. By properly selecting the volume of the biological fluid, the flow rate of the restrictive flow channel, and the volume of the cell retention region, the rotor can be designed to allow separation of a predetermined fluid volume without substantial carryover of the cellular components.

In an alternate method, the cell-containing biological fluid is transferred to a mixing chamber where it is combined with a diluent. The biological fluid and diluent are mixed in the mixing chamber, typically by reversing the rotational direction of the rotor or by alternately accelerating and decelerating the velocity of rotation in a single rotational direction. The cells can then be separated outward into a peripheral retention region by spinning the rotor. A flow restrictive outlet on the mixing chamber assures that there is sufficient residence time to effect a desired degree of separation. Optionally, the fluid from the mixing chamber flows through the restrictive channel and into a separation chamber as described above. In this way, two stages of separation are achieved, assuring substantially complete separation of cellular components.

BRIEF DESCRIPTION OF THE DRAWINGS

FIG. 5 is a cross-secrionai view similar to FIG. 3, illustrating an alternate embodiment of the separation chamber including a cell trap.

FIG. 6 is a plan view of an alternate rotor design.

FIG. 7 is a cross-sectional view taken along line 7—7 of FIG. 6.

FIG. 8 is a cross-sectional view taken along line 8—8 of FIG. 6.

FIG. 9 is a plan view of a second alternate rotor design.

FIG. 10 is a cross-sectional view taken along line 10—10 in FIG. 9.

DESCRIPTION OF THE SPECIFIC EMBODIMENTS

Figure 1:
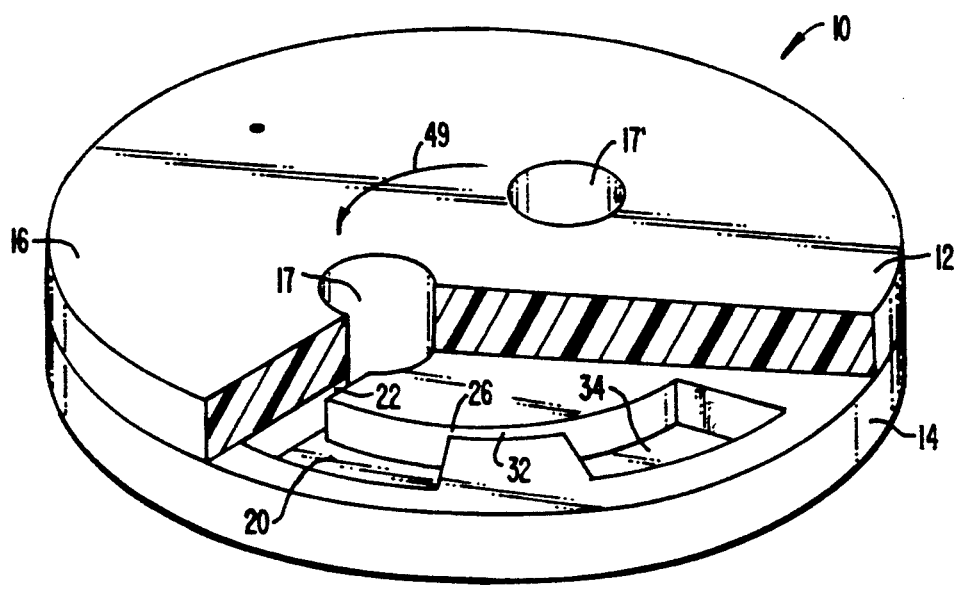
FIG. 1 is a perspective view of an analytical rotor constructed in accordance with the principles of the present invention, with portions broken away.

The present invention provides apparatus and methods for separating cellular components from biological fluids, and in particular for separating blood cells from whole blood to provide cell-free plasma which may then be subjected to a wide variety of analytic procedures. Although the present invention is particularly suitable for separating blood cells from blood to produce plasma, it will also be useful with numerous other biological fluids, such as urine, sputum, semen, saliva, ocular lens fluid, cerebral fluid, spinal fluid, amniotic fluid, and tissue culture media, as well as food and industrial chemicals, and the like, where it may be desirable to separate cells and other interfering substances prior to analysis or assay.

The present invention provides for the separation of one or more aliquots or portions of the biological fluid into a cellular fraction which is retained within a cellular retention region within the rotor and a cell-free fluid fraction which is delivered to collection and/or analysis chambers. Conveniently, the cell-free fluid fraction may undergo reaction(s) within the analysis chambers, e.g., reaction with a reagent which forms part of an analytical procedure to detect one or more analytes within the fluid. The cell-free liquid fraction may further be optically analyzed while present in the rotor, either with or without prior reaction.

The apparatus of the present invention comprises an analytical rotor having a rotor body which is capable of being mounted on a conventional laboratory centrifuge of the type which is commercially available from suppliers, such a Beckman Instruments, Inc., Spinco Division, Fullerton, Calif.; Fisher Scientific, Pittsburgh, Pa.; VWR Scientific, San Francisco, Calif., and the like. Generally, the centrifugal rotor will include a receptacle or other coupling device suitable for mounting on a vertical drive shaft provided by the centrifuge. The particular design of the receptacle or coupling device will depend on the nature of the centrifuge, and it will be appreciated that the centrifugal rotor of the present invention may be adapted for use with all or most types of centrifuges which are now available or which may become available in the future.

The rotor body comprises a structure which maintains a desired geometric pattern or relationship between a plurality of chambers, interconnecting passages, and vents, as described in more detail hereinbelow. Usually, the body will be a substantially solid plate or disk with the chambers and passages formed as spaces or voids in the otherwise solid matrix. Conveniently, such solid plate structures may be formed by laminating a plurality of separately-formed layers together into a composite structure where the chambers and horizontal passages are generally formed between adjacent layers. The vertical passages may be formed through the layers. The individual layers may be formed by injection molding, machining, or combinations thereof, and will usually be joined together, typically using a suitable adhesive or by ultrasonic welding. The final enclosed volumes are formed when the layers are brought together. Of course, the centrifugal rotor could also be formed as a plurality of discrete components, such as tubes, vessels, chambers, etc., arranged in a suitable framework. Such assemblies of discrete components, however, are generally more difficult to manufacture and are therefore less desirable than those formed within a substantially solid plate.

The rotor body may be formed from a wide variety of materials and may optionally include two or more materials. Usually, the material(s) will be transparent so that the presence and distribution of the biological fluid, cellular components, and reagents, may be observed within the various internal chambers and passages. Optionally, to the extent analytical chambers, e.g., cuvettes, or other test wells are formed within the rotor, it is desirable to have suitable optical paths formed within the rotor so that the contents of the cuvettes may be observed spectrophotometrically, fluorometrically, or by other optical assessment instruments. The construction of suitable cuvettes having particular optical paths formed therethrough is disclosed in copending application Ser. No. 07/678,823, the disclosure of which has previously been incorporated herein by reference. In the preferred embodiment, the rotor is formed with an acrylic resin having suitable optical properties, at least in those areas which define an optical path.

The apparatus and method of the present invention are suitable for performing a wide variety of analytic procedures and assays which are beneficially or necessarily performed on blood plasma. The analytic procedures may require that the blood plasma be combined with one or more reagents so that some visibly detectable change occurs in the plasma which may be related to the presence and/or amount of a particular component (analyte) or characteristic of the plasma. Preferably, the plasma will undergo a reaction or other change which results in a change in color, fluorescence, luminescence, or the like, which may be measured by conventional spectrophotometers, fluorometers, light detectors, etc. In some cases, immunoassays and other specific binding assays may be performed within the cell-free fluid collection chamber or within cuvettes which are connected to the collection chamber. Generally, such assay procedures should be homogenous and not require a separation step. In other cases, however, it may be possible to accommodate heterogenous assay systems by providing a means to separate blood plasma from the collection chamber or another test well or cuvette after the immunological reaction step has occurred.

Conventional blood assays which may be performed include glucose, lactate dehydrogenase, serum glutamic-oxaloacetic transaminase (SGOT), serum glutamic-pyruvic transaminase (SGPT), blood urea (nitrogen) (BUN), total protein, alkalinity, phosphatase, bilirubin, calcium, chloride, sodium, potassium, magnesium, and the like. This list is not exhaustive and is intended merely as being exemplary of the assays which may be performed using the apparatus and method of the present invention. Usually, these tests will require that the blood and plasma be combined with one or more reagents which result in an optically detectable, usually photometrically detectable, change in the plasma. The reagents which are required are well known and amply described in the patent and scientific literature.

Figure 2:
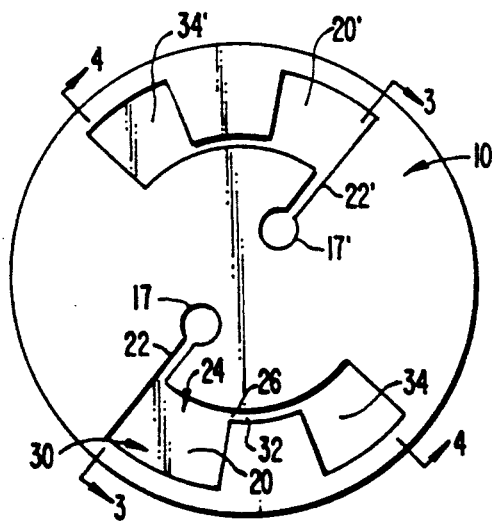
FIG. 2 is a plan view of the centrifugal rotor of FIG. 1.
Figure 3:
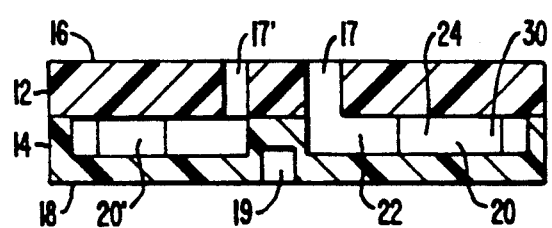
FIG. 3 is a cross-sectional view taken along line 3—3 of FIG. 2.
Figure 4:
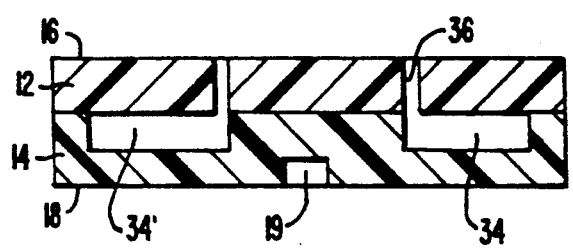
FIG. 4 is a cross-sectional view taken along line 4—4 of FIG. 2.

Referring now to FIGS. 1-4, an analytical rotor 10 constructed in accordance with the principles of the present invention will be described in detail. The rotor 10 is in the form of a substantially solid disk including a top layer 12 laminated to a bottom layer 14 to form a composite structure. Typically, each of the layers 12 and 14 will be composed of the same material, usually a transparent plastic such as an acrylate, but it is possible that the layers will be composed of different materials and that each layer may include two or more different materials forming different portions of that layer. The exposed surface 16 will be referred to hereinafter as the top surface while the exposed surface of the bottom layer 14 will be referred to as the bottom surface 18.

The rotor 10 includes a mounting receptacle 19 formed in the bottom surface 18 of lower layer 14. The mounting receptacle 19 is suitable for mounting the rotor 10 on the spindle of a conventional centrifuge (not shown), as described hereinabove.

A first separation assembly within the rotor 10 includes a sample receptacle 17 formed through the top layer 12 and into the bottom layer 14 which is joined to a separation chamber 20 by a flow restrictive channel 22. The separation chamber 20 includes a radially inward region 24 which generally defines a fluid flow path from the entry point of the flow channel 22 to a fluid outlet port 26. The separation chamber further includes a radially outward region 30 which forms a cell retention region which receives cells which are separated from the biological fluid as the rotor 10 is spun.

As illustrated, rotor 10 includes a second separation assembly including sample receptacle 17'; separation chamber 20', flow restrictive channel 22', and collection chamber 34'. The chambers and passageways in the second separation assembly are arranged in a pattern identical to that of the first separation assembly so that two equivalent separation and analytic procedures may be performed simultaneously. It will be appreciated that the rotor could be adapted to include three or more similar or identical separation assemblies to allow additional separation procedures to be performed simultaneously.

It is necessary that the point at which flow channel 22 enters the separation chamber 20 be annularly-spaced apart from the collection port 26. In this way, the biological fluid will have a sufficient residence time within the separation chamber as the fluid flows from the entry point to the collection port. In the preferred embodiment, the flow passage 22 will be connected at one annular extremity of the collection chamber 20 while the collection port 26 will be located at or near the other annular extremity.

Usually, the receptacle 17 will be sized to receive the entire volume of biological fluid which is to be separated. The cell retention region 30 within the separation chamber 20 will be sized to accommodate the maximum possible volume of cellular material which may be present in the sample. For blood samples, this will depend on the blood volume as well as the maximum expected hemocrit to be processed. Usually, the cell retention region will have a volume which is equal to about 4% to 10%, more usually being about 7%, of the volume of the sample region 18.

The dimensions of the flow channel 22 will be selected to provide a flow rate of the biological sample into the separation chamber 20 which is sufficiently low to allow time for the cellular components to be separated from the fluid prior to the fluid reaching the outlet port 26. The particular dimensions will depend, of course, on the precise characteristics of the fluid as well as the speed at which the rotor is to be spun. For most purposes, flow channel having a width in the range from about 0.1 to 0.4 mm, more usually from about 0.15 to 0.25 mm, and a depth in the range from about 0.01 to 0.2 mm, more usually in the range from about 0.03 to 0.06 mm, will be suitable.

The outlet port 26 may be connected to an annular overflow passage 32 which in turns is connected to an annularly spaced-apart collection chamber 34. Thus, after sufficient sample has entered the separation chamber 20 to fill the chamber 20 back to the inner peripheral wall thereof, cell-free fluid will begin flowing laterally through the connecting channel 32 into the collection chamber 34. It will be appreciated that initially, the separation chamber 20 will be filled primarily with cell-free fluid, having a thin layer of separated cells formed adjacent the outer peripheral wall of the chamber. Over time, however, the thickness of the layer of cells will increase, with the interface between cells and the cell free fluid moving radially inward over time. The volume of the separation chamber 20, however, will be sufficient so that the entire sample will be separated before the cellular interface can move sufficiently close to the outlet port 26 to cause overflow of the cellular material.

The cell-free fluid entering chamber 34 will be available immediately to react with any reagents which may be present within the chamber. In this way, an analytical reaction may be initiated prior to complete separation of the biological fluid. By the time the separation is complete, the desired analytical reaction may be substantially completed, requiring only a small additional reaction time. Optionally, the cell-free fluid within collection chamber 34 may be observed directly through the rotor 10 without removal from the chamber 34.

A vent port 36 will normally be provided near the inner peripheral wall of the collection chamber 34 in order to allow gases to vent as the chamber is filled with fluid.

The rotor 10 is used by applying a biological sample to be separated into sample receptacle 17, usually while the rotor is at rest. The rotor 10 is then spun on a conventional centrifuge, typically at a speed in the range from about 1,500 rpm to 5,000 rpm, more usually being in the range from about 2,500 to 4,000 rpm, for a time in the range from about 20 seconds to five minutes, depending on the volume of fluid being separated. The direction of rotation is not critical but will usually be counterclockwise (i.e., the direction of arrow 49 in FIG. 1) so that cellular build-up will be more likely to move away from the outlet port 26. Cell-free fluid will begin entering the collection chamber 34 as soon as the level of fluid in the separation chamber 20 has moved radially inward to reach the collection port 26. The collection chamber 34 may include reagent(s) which are selected to effect desired detection reactions, and reaction with the reagents may begin as soon as the cell-free fluid enters the collection chamber while the rotor continues to spin and additional fluid continues to be separated.

Referring now to FIG. 5, an alternate embodiment of the separation chamber 40 is illustrated. The separation chamber 40 includes a cell retention region 42 which is separated from the remainder of the separation chamber by a capillary flow restriction 44. In this way, cells may pass radially outward from the flow path region 46 through the capillary restriction 44 as the rotor is spun but will be unable to pass backward through the restriction after the spinning has stopped. Thus, the cells will be effectively trapped within the retention region 42, even if the rotor is subjected to rough handling which might cause back flow of the cells in an embodiment which did not include the capillary restriction.

Referring now to FIGS. 6–8, a second embodiment 50 of the analytical rotor of the present invention is illustrated. The second embodiment 50 comprises a disk-shaped rotor body similar to the first embodiment 10. A sample receptacle 52 is connected to a separation chamber 54 by means of a flow restrictive channel 56. Separation chamber 54 includes a cell retention region 58 at its outer periphery and a collection port 60 located near its inner periphery. The collection port 60 is annularly spaced apart from the inlet of the flow restrictiv channel 56 in order to allow a sufficiently long flow path to provide sufficient residence time for the desired cellular separation.

The collection port 60 is vertically disposed and connected to an underlying collection chamber 62 which in turn is connected to a plurality of analytical cuvettes 64 located about the periphery of the rotor 50. A vent path 66 will be provided in order to allow gases to escape from the separation chamber 54 as the fluid enters.

In use, a biological sample is introduced to the sample receptacle 52, and the rotor is spun to cause the sample to enter the separation chamber 54 where the cellular components collect in the retention region 58. After a short time, cell-free fluid will reach the collection port 60 and will begin to flow downward into the collection chamber 62. From the collection chamber, the cell-free fluid will move radially outward into the individual cuvettes where it may undergo reaction and subsequent analysis.

Referring now to FIGS. 9 and 10, a third embodiment 70 of the analytical rotor of the present invention will be described. The analytical rotor 70 comprises a disk-shaped rotor body 72 generally similar to the rotor 10 and rotor 50 described previously. The rotor 70 comprises a sample receptacle 74 having an inlet port 76. A diluent chamber 78 is formed adjacent the sample chamber 74 and will typically hold a container of "prepackaged" diluent. Conveniently, the diluent container will be introduced at the time of rotor fabrication, but means may be provided for inserting such containers immediately prior to use.

A mixing chamber 80 is located radially outward from both the sample chamber 74 and diluent chamber 78. The sample chamber 74 is connected to the mixing chamber 80 through a port 82, and the diluent chamber 78 is connected to the mixing chamber 80 through a port 84. Both the ports 82 and 84 are sufficiently large so that flow will not be substantially restricted between the chambers 74 and 78 and the mixing chamber 80. Thus, after introduction of the sample to be tested and the diluent, both the sample and the diluent may be substantially immediately transferred to the mixing chamber 80 by spinning the rotor 70.

The mixing chamber 80 is connected to separation chamber 86 by a flow restrictive channel 88. The flow restrictive channel 88, typically a capillary channel, will prevent immediate transfer of the contents of mixing chamber 80 to the separation chamber 86. Thus, the sample and the diluent may be thoroughly mixed while present in chamber 80, typically by reversibly rotating the rotor 70 or by alternately accelerating and decelerating the velocity of rotation in a single direction. An exemplary pattern of reversible rotation is to accelerate from 0 to 1200 rpm in a first rotational direction over a period of three seconds, followed by stopping the rotation and accelerating from 0 to 1200 rpm in the opposite rotational direction over a period of three seconds. Such a pattern can be repeated until the desired mixing is achieved, with five repetitions usually being sufficient. An exemplary pattern of acceleration and deceleration is to spin the rotor 70 at 500 rpm for a short period, e.g., about 1.6 seconds, followed by rapid acceleration to 4000 rpm for about 1.6 seconds. This pattern of accleration and deceleration will also be repeated a sufficient number of times to effect a desired degree of mixing.

Conveniently, the mixing chamber 80 may itself be formed as a separation chamber including a cell retention region 90 (best illustrated in FIG. 10) at its radially outward periphery. The cell retention region 90 is isolated by a capillary restriction 92, similar to restriction 44 described in connection with FIG. 5. Thus, after mixing of the sample and diluent is completed, a first stage of cellular separation may be effected by spinning the rotor to cause the more dense cells to flow through capillary restriction 92 into the cell trap 90.

While a substantial proportion of the cellular components may be removed as just described in the mixing chamber 80, the fact that the mixing chamber is filled and agitated prior to separation increases the likelihood that there will be carryover of cellular material from the mixing chamber. Thus, a separation chamber similar to chambers 20 and 40 described previously is still necessary. The flow restrictive channel 88 is connected to a first annular extremity 92 of the separation chamber 86, while an outlet channel 94 is connected to the opposite annular extremity. A cell retention region 96 is formed at the radially outward periphery of chamber 86, so that cell-containing fluid entering the chamber through flow restrictive channel 88 will have sufficient residence time for the cellular material to separate out into the cell retention region 96 as the rotor is spun.

The flow restrictive channel 88 will have an inlet port 98 (opening into separation chamber 86) which is spaced radially-outward from the outlet port 100 (which is connected to the mixing chamber 80). Thus, rotation of the rotor 70 will cause a fluid to flow at a controlled rate from the mixing chamber 80 to the separation chamber 86.

In a preferred aspect of the present invention, the flow restrictive channel 88 may include a siphon structure defined by a path segment 102 which extends radially inward. Such a siphon structure will initially prevent flow from the mixing chamber 80 to the separation chamber 86. That is, so long as the path 92 is not filled with liquid, spinning of rotor 70 will not cause fluid from mixing chamber 80 to flow radially inward around the path 102 which defines the size and structure. Once spinning of the rotor 70 is stopped, however, capillary forces will cause fluid from the mixing chamber 80 to fill the flow restrictive channel 88, as described in connection with the previous embodiments. Once the channel 88 is filled, spinning of the rotor 70 will then cause fluid to flow without interruption from the mixing chamber 80 to the separation chamber 86. Use of the siphon structure is advantageous since it inhibits flow of the sample and diluent during the initial transfer from the sample chamber 74 and diluent chamber 78 which is effected by high speed spinning. Some carryover may occur, however, during the subsequent agitation step.

In use, a biological sample is introduced to sample receptacle 74 through port 76. Diluent will either be introduced or will be present in a package within the diluent chamber 78. In some cases, it may be necessary to open or pierce a diluent container in order to allow transfer of the diluent to the mixing chamber 80. In any event, the rotor 70 is then spun in order to effect transfer of the sample and diluent into the mixing chamber 80. At this point, the siphon structure in the flow restrictive channel 88 will substantially prevent any flow or carryover of fluids into the separation chamber 86.

After the transfer of sample and diluent to the mixing chamber 80 has been completed, the contents of the chamber will be thoroughly mixed by subjecting the rotor 70 to a constantly reversing rotation or by alternately increasing and decreasing the velocity of rotation in the same direction, as described above. Such agitation will be continued for a time sufficient to assure complete mixing of the diluent sample. During such agitation, there may be some inadvertent loss or transfer of fluid from the mixing chamber 80 into the separation chamber 86, although the flow restrictive nature of channel 88 as well as the presence of the siphon structure will largely inhibit such transfer.

After the mixing is complete, the rotor 70 is held stationary for a time sufficient to allow fluid from the mixing chamber 80 to fill the flow restrictive channel 88 by capillary action. Once the channel 80 is filled, the rotor can be spun in order to effect the fluid flow from the mixing chamber to the separation chamber 86 by centrifugal force. The separation chamber 86 will fill with the fluid from the mixing chamber 80, and any cells which may be present will be trapped within the cell retention region 96, in a manner similar to that described for previous embodiments. Cell-free fluid from the separation chamber 86 will then flow into the distribution channel 92 and into a plurality of analytical chambers 104, e.g., optical cuvettes as described previously.

Although the foregoing invention has been described in detail for purposes of clarity of understanding, it will be obvious that certain modifications may be practiced within the scope of the appended claims.

What is claimed is:

1. An analytical rotor for continuously separating fluid from a cell-containing liquid sample, said rotor comprising a rotor body having an axis of rotation, a sample chamber, a separation chamber, a cell retention region located generally at the radially outward periphery of the separation chamber, a flow restrictive channel connecting the sample chamber to the separation chamber, and means annularly offset from the flow restrictive channel and radially inward from the cell retention region for collecting cell-free fluid from the separation chamber, whereby spinning the rotor causes liquid sample in the sample chamber to flow into the separation chamber where cells in the sample move radially outward into the retention region and cell-free fluid flows annularly into the collecting means, wherein said flow restrictive channel and said collecting means are annularly separated by a distance sufficient to permit cells to separate from the fluid before the fluid reaches the collecting means.

2. An analytical rotor as in claim 1, wherein the sample chamber is a sample receptacle having a port for receiving the sample.

3. An analytical rotor as in claim 1, wherein the sample chamber is a mixing chamber having a volume greater than that of the separation chamber.

4. An analytic rotor as in claim 3, further comprising a sample receptacle and a diluent chamber spaced radially-inward from the mixing chamber and non-flow-restrictive means for connecting the sample receptacle and the diluent chamber to the mixing chamber, whereby sample in the sample receptacle and diluent in the diluent chamber may be rapidly transferred in a radially outward direction to the mixing chamber but will be retained in the mixing chamber by the flow restrictive channel.

5. An analytical rotor as in claim 3, wherein the mixing chamber includes a cell retention region at a radially-outward periphery thereof.

6. An analytical rotor as in claim 1, wherein the means for collecting cell-free fluid comprises a collection chamber and an overflow channel connecting the collection chamber to the separation chamber.

7. An analytical rotor as in claim 6, wherein a reagent is disposed within the collection chamber.

8. An analytical rotor as in claim 6, wherein the collection chamber defines an optical path to allow analysis of the contents of the collection chamber.

9. An analytical rotor as in claim 1, wherein the means for collecting cell-free fluid comprises a drain port within the separation chamber and a collection chamber beneath the drain port.

10. An analytical rotor as in claim 1, wherein the flow restrictive channel is connected to the sample chamber at a location within the sample chamber furthest from the axis of rotation.

11. An analytical rotor as in claim 1, wherein the flow restrictive channel is connected to the separation chamber at one annular extremity thereof and the means for collecting cell-free fluid is connected to the separation chamber at the other annular extremity thereof.

12. An analytic rotor as in claim 1, wherein the flow restrictive channel is substantially straight.

13. An analytical rotor as in claim 1, wherein the flow restrictive channel includes a siphon structure having a path segment which extends radially inward.

14. An analytical blood separator comprising:
a rotor having top and bottom surfaces and a central axis;
a sample receptacle open to the top surface of the rotor and having an outlet port at a location therein which is furthest from the central axis;
an annularly-shaped separation chamber located radially outward from the sample receptacle and having an inner peripheral wall, an outer peripheral wall, a first annular extremity, a second annular extremity, and an inlet port located near the first annular extremity;
a flow restrictive channel connecting the outlet port of the sample receptacle to the inlet port of the separation chamber; and
means near the inner peripheral wall and second annular extremity within the separation chamber for collecting blood plasma.

15. An analytical blood separator as in claim 14, wherein the rotor is a disk having means for mounting on a driver.

16. An analytical blood separator as in claim 15, wherein the means for collecting blood plasma comprises an annularly-shaped collector chamber and an overflow channel connecting the collection chamber to the second chamber extremity of the separation chamber.

17. An analytical blood separator as in claim 16, wherein the collection chamber has an inner peripheral wall which is aligned on a common diameter with the overflow channel and the inner peripheral wall of the separation chamber.

18. An analytical blood separator as in claim 15, wherein the means for collecting blood plasma comprises a drain port within the separation chamber and a collection chamber beneath the drain port.

19. An analytical blood separator comprising:
a rotor having top and bottom surfaces and a central axis;
a sample receptacle open to the top surface of the rotor and having an outlet port at a location therein which is furthest from the central axis;
a diluent chamber having an outlet port at a location therein which is furthest from the central axis;
a mixing chamber located radially outward from both the sample receptacle and the diluent chamber and connected thereto through said respective outlet ports;
a separation chamber located radially outward from the mixing chamber;
a flow restrictive channel connecting the mixing chamber to the separation chamber; and
means within the separation chamber and annularly offset from the flow restrictive channel for collecting cell-free fluid.

20. An analytical blood separator as in claim 19, wherein the separation chamber is disposed annularly having an inner peripheral wall, an outer peripheral wall, a first annular extremity, and a second annular extremity, wherein the flow restrictive channel is connected along the first annular extremity and the cell-free fluid collecting means is located near the inner peripheral wall and second annular extremity.

21. An analytical blood separator as in claim 19, wherein the mixing chamber is disposed annularly within the rotor and includes a cell retention region at its outward periphery.

22. An analytical blood separator as in claim 19, wherein the means for collecting cell-free fluid includes a plurality of annularly spaced-apart analysis chambers.

23. An analytical blood separator as in claim 19, wherein the flow restrictive channel is substantially straight.

24. An analytical rotor as in claim 19, wherein the flow restrictive channel includes a siphon structure having a path segment which extends radially inward.

25. A method for separating cells from a biological fluid, said method comprising:
    introducing the fluid into a receptacle region within a rotor;
    spinning the rotor to effect radially outward flow of the fluid from the receptacle region through a flow restrictive passage into a separation chamber, whereby cells collect in a retention region at the radially outward periphery of the separation chamber; and
    continuously removing the resulting cell-free fluid through a port which is disposed at a position located radially inward from the retention region and annularly displaced from the flow restrictive passage.

26. A method as in claim 25, wherein the biological fluid is blood and the cell-free fluid is plasma.

27. A method as in claim 25, wherein the port is connected to an annular channel which allows the cell-fluid to pass to an annularly-displaced collection chamber.

28. A method as in claim 25, wherein the port is connected to a vertical passage which allows the cell-free fluid to pass to a vertically-displaced collection chamber.

29. A method as in claim 25, further comprising exposing the cell-free fluid to a reagent after the fluid is removed through the port.

30. A method as in claim 29, further comprising examining the cell-free fluid after exposure to the reagent.

31. A method as in claim 25, wherein the biological fluid continues to be introduced to the receptacle region while the cell-free fluid is removed through the port.

32. A method for mixing and separating plasma from a whole blood sample, said method comprising:
    introducing the blood sample to a receptacle region within a rotor;
    spinning the rotor to effect radially outward flow of the sample and a diluent into a mixing chamber;
    agitating the sample and diluent within the mixing chamber to form a mixture;
    spinning the rotor to effect radially outward flow of the mixture from the mixing chamber through a flow restrictive passage into a separation chamber, whereby blood cells collect in a retention region at the radially outward periphery of the separation chamber; and
    continuously removing the resulting cell-free plasma through a port which is disposed at a portion located radially inward from the retention region and annularly displaced from the flow restrictive passage.

33. A method as in claim 32, wherein the cell-free plasma flows through the port into a plurality of annularly spaced-apart analysis chambers.

34. A method as in claim 32, further comprising spinning the rotor while the mixture is in the mixing chamber, whereby blood cells collect in a retention region at the radially outward periphery of the mixing chamber.

35. A method as in claim 32, further comprising stopping the rotor after the mixture is formed to allow the mixture to enter the flow restrictive passage, wherein said flow restrictive passage is at least partly a capillary having a siphon formed therein.

36. An analytical rotor for mixing and separating fluid from a cell-containing liquid, said rotor comprising:
    a rotor having top and bottom surfaces and a central axis;
    a sample receptacle open to the top surface of the rotor and having an outlet port at a location therein which is furthest from the central axis;
    a diluent chamber having an outlet port at a location therein which is furthest from the cental axis;
    a mixing chamber located radially outward from both the sample receptacle and the diluent chamber and connected thereto through said respective outlet ports, wherein the mixing chamber is disposed annularly within the rotor and includes a cell retention region at its outer periphery; and
    means connected to the mixing chamber for draining said mixing chamber for draining said mixing chamber at a rate selected to provide sufficient residence time for the cells to separate from the combined sample and diluent prior to draining.

37. An analytical rotor as in claim 36, wherein the means for draining the mixing chamber comprises a flow restrictive channel.

38. An analytical rotor as in claim 36, wherein the means for draining the mixing chamber comprises a siphon structure having a path segment which extends radially inward.

39. An analytical rotor as in claim 36, wherein the means for draining the mixing chamber is further connected to a plurality of annularly spaced-apart analysis chambers.

40. A method for mixing and separating fluid from a cell-containing liquid, said method comprising:
    introducing a cell-containing liquid sample to a receptacle region within a rotor;
    spinning the rotor to effect radially outward flow of the sample and a diluent into a mixing chamber;
    agitating the sample and diluent within the mixing chamber to form a mixture; and
    spinning the rotor to cause radially outward flow of the cells into a retention region while the remaining fluid flows from the chamber through a flow restrictive passage which allows sufficient fluid residence time within the chamber to achieve a desired separation.

41. A method as in claim 40, wherein the cell-containing liquid is blood.

42. A method as in claim 40, wherein the fluid flows through the flow restrictive passage into a separation chamber having a cell retention region at its radially outward periphery, whereby any cells carried over will be separated.

43. A method as in claim 40, wherein the cell-free fluid flows from the flow restrictive channel to a plurality of spaced-apart analysis chambers 44. A method as in claim 40, further comprising stopping the rotor after the mixture is formed to allow the mixture to enter the flow restrictive passage, wherein said flow restrictive passage is at least partly a capillary having a siphon formed therein.

* * * * *